United States Patent [19]

Desai et al.

[11] Patent Number: 5,028,616

[45] Date of Patent: Jul. 2, 1991

[54] N-BENZYLPIPERIDINE AMIDES

[75] Inventors: Bipinchandra N. Desai, Vernon Hills; Kerry W. Fowler, Chicago, both of Ill.

[73] Assignee: G. D. Searle & Co., Chicago, Ill.

[21] Appl. No.: 402,951

[22] Filed: Sep. 5, 1989

[51] Int. Cl.$^5$ .................. A61K 31/445; C07D 405/12
[52] U.S. Cl. .................. 514/321; 514/329; 546/197; 546/224
[58] Field of Search .............. 514/321, 329; 546/197, 546/224

[56] References Cited

U.S. PATENT DOCUMENTS

| | | | |
|---|---|---|---|
| 3,907,810 | 9/1975 | Cavalla | 546/210 |
| 3,910,931 | 10/1975 | Cavalla | 546/206 |
| 3,910,932 | 10/1975 | Cavalla | 546/194 |
| 3,912,741 | 10/1975 | Cavalla | 546/202 |
| 3,917,614 | 11/1975 | Cavalla | 546/208 |
| 3,919,242 | 11/1975 | Cavalla | 546/197 |
| 4,028,365 | 6/1977 | Cavalla | 546/200 |
| 4,029,801 | 6/1977 | Cavalla | 514/329 |
| 4,045,444 | 8/1977 | Cavalla | 546/197 |
| 4,046,767 | 9/1977 | Cavalla | 546/197 |
| 4,138,492 | 2/1979 | Noverola | 546/194 X |
| 4,277,501 | 7/1981 | Melloy | 514/654 |
| 4,289,781 | 9/1981 | Bengtsson | 546/200 X |
| 4,596,827 | 6/1986 | Melloy | 514/605 |

FOREIGN PATENT DOCUMENTS 1345872 2/1974 United Kingdom .

OTHER PUBLICATIONS

Fleming, J. S. et al., "Effects of . . . Anti-Hypertensive Agent . . ." *Federation Proceedings*, vol. 43, p. 553, 1984.

*Primary Examiner*—Robert W. Ramsuer
*Assistant Examiner*—Jacqueline Haley
*Attorney, Agent, or Firm*—Joy Ann Serauskas; Paul D. Matukaitis

[57] ABSTRACT

N-benzylpiperidine amides, which have activity as Class III antiarrhythmic agents, acting by prolonging cardiac action potential repolarization. The invention further provides for compositions incorporating the compounds and methods of their use, as well as providing for pharmaceutically acceptable salts of the compounds.

15 Claims, No Drawings

N-BENZYLPIPERIDINE AMIDES

BACKGROUND OF THE INVENTION

The present invention provides novel compounds, novel compositions, methods of their use and methods of their manufacture, such compounds pharmacologically useful in the treatment of cardiac arrhythmias. More specifically, the compounds of the present invention are Class III antiarrhythmic agents which, by effectively prolonging repolarization of a cardiac cell action potential, can be used effectively to treat certain cardiac arrhythmias.

Antiarrhythmic drugs have been grouped together according to the pattern of electrophysiological effects that they produce and/or their presumed mechanisms of action. Thus, Class I antiarrhythmic agents are characterized by being sodium channel blockers. Class II antiarrhythmic agents are beta-adrenergic blockers, Class III antiarrhythmic agents prolong repolarization, and Class IV antiarrhythmic agents are calcium channel blockers. Currently, there are very few Class III antiarrhythmic agents available for theraputic use. Among them is bretylium. Bretylium's usefulness is limited, however, and currently its theraputic use is reserved for life-threatening ventricular arrhythmias that are refractory to other therapy. Thus, bretylium's use is generally confined to intensive care units. It is an object of this invention to provide Class III antiarrhythmic agents of broader therapeutic use than existing Class III antiarrhythmic agents.

SUMMARY OF THE INVENTION

The invention relates to novel compounds of the general formula I:

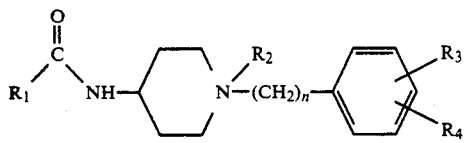

the pharmaceutically acceptable non toxic salts thereof, and the hydrated forms thereof wherein $R_1$ is phenyl, phenyl substituted by one or more independently of alkyl of from one to ten carbon atoms, halogen, amino or alkoxy of from one to ten carbon atoms, phenyl substituted phenyl, alkyl of from one to ten carbon atoms cycloalkyl of three to eight carbon atoms, or benzodioxolyl; $R_2$ is alkyl of from zero to ten carbon atoms in length; n is an integer of from zero to three; and $R_3$ and $R_4$ are independently hydrogen, halogen, halogen substituted alkyl of from one to ten carbon atoms in length, arylalkoxy of from one to ten carbon atoms in length, or alkoxy of one to ten carbon atoms in length with the proviso that $R_3$ and $R_4$ cannot both be H when $R_1$ is 2-methoxy, 4-amino, or 5-chloro phenyl.

The compounds and pharmaceutical compositions thereof are useful in the antiarrhythmic methods of the invention. The invention further provides dosage unit forms adapted for oral, topical and parenteral administration. Also provided for in this invention are the pharmaceutically acceptable salts of the compounds.

DETAILED DESCRIPTION OF THE INVENTION

The term "benzodioxole" is defined to mean the substituent of the formula

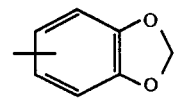

As used herein, the expression "alkoxy" is defined to include alkyl of one to ten carbon atoms. The term "alkyl" is defined to include straight or branched carbon-carbon linkages of one to ten carbon atoms. The term "aryl" shall include phenyl and phenyl substituted by alkyl of from one to ten carbon atoms in length, or substituted by halogen.

The term "halogen" shall include chlorine, bromine, iodine and fluorine.

The term "cardiac arrhythmia" is defined to mean any variation from the normal rhythm of the heartbeat, including, without limitation, sinus arrhythmia, premature heartbeat, heartblock, fibrillation, flutter, pulsus alternans, tachycardia, paroxysmal tachycardia and premature ventricular contractions.

The term "repolarization of cardiac cells" is defined as those phases of a cardiac action potential during which time a depolarized cardiac cell is reverting to normal pre-polarization transmembrane voltage.

The term "pharmaceutically acceptable salts" refers to non-toxic salts of the compounds of this invention which are generally prepared by reacting the free base with a suitable organic or inorganic acid. Representative salts include the hydrochloride, hydroiodic, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts.

Compounds of the invention can be prepared readily according to the following reaction scheme or modifications thereof using readily available starting materials, reagents and conventional synthesis procedures. In these reactions, it is also possible to make use of variants which are in themselves known, but are not mentioned in greater detail.

Scheme 1

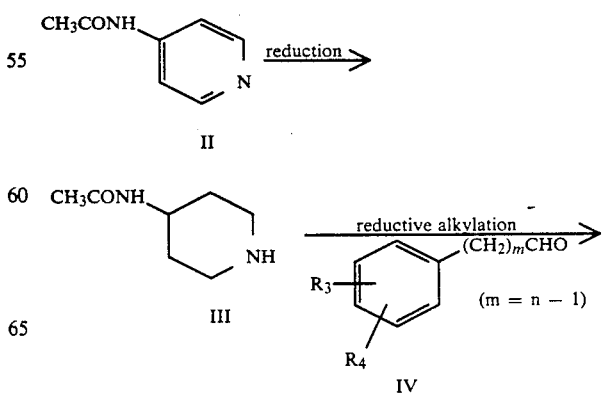

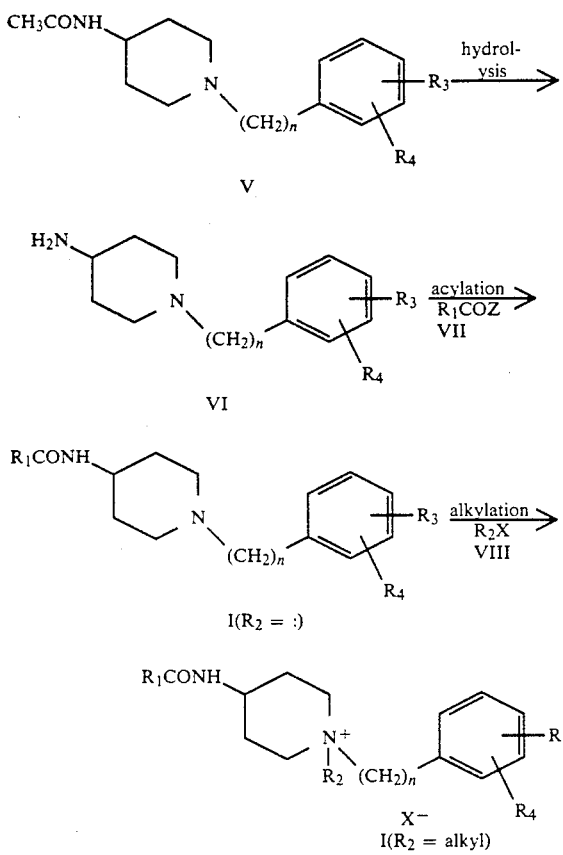

In the above scheme, $R_1$, $R_2$, $R_3$, and $R_4$ all defined as before, while COZ in structure VII denotes use of an acylating agent selected from the group consisting of a carboxylic acid chloride, a carboxylic acid activated as the mixed anhydride, or the carboxylic ester activated by alkylaluminum reagents.

Reduction of 4-acetamidopyridine Formula II affords 4-acetamidopiperidine Formula III. A method for the preparation of 4-acetamidopiperidine III involves the reduction of 4-acylamino N-benzyl pyridinium compounds by alkali metal hydrides or catalytic hydrogenation of the aromatic ring with debenzylation as described in U.K. 1,537,867 (G. O. Weston) and U.K. 1,345,872 (J. L. Archibald and J. F. Cavalla) the entire disclosure of which is incorporated herein by reference. Preferred reduction conditions employ a ruthenium on carbon catalyst in a solvent such as alcohol, tetrahydrofuran (THF), or acetic acid under an atmosphere of hydrogen. Subsequent reductive alkylation of the piperidine Formula III with aldehydes Formula IV provides the N-alkylated intermediates Formula V. Preferred conditions employ Pt/C catalyst in an inert solvent such as alcohol, THF, or acetic acid under an atmosphere of hydrogen. Alternative preferred conditions employ borane-pyridine complex as the reducing agent at room temperature in alcohol, acetic acid or methylene chloride. Hydrolysis of the amide bond of acetamides Formula V provides amine intermediates Formula VI. Although hydrolysis may be effected in acid or base, the preferred method employs hydrolysis in 1.2 M HCl at 100° C. Alternative preferred acylating conditions leading to amides ($R_2$=alone electron pair) employ a carboxylic acid chloride, a carboxylic acid activated as the mixed anhydride, or the carboxylic ester activated by alkylaluminum reagents.

The amides Formula I are subsequently converted to the quaternary salts Formula I (where $R_2$ is not an unshared valence bond) by N-alkylating reagents $R_2X$ Formula VIII (where X is a suitable leaving group such as halogen, mesylate, or tosylate) in an inert solvent. Preferred alkylation conditions employ acetonitrile as the solvent at room temperature.

The compounds of the present invention can be administered in such oral dosage forms as tablets, capsules, pills, powders, granules, elixers, tinctures, suspensions, syrups and emulsions. Likewise, it can also be administered in intravenous, intraperitoneal, subcutaneous or intramuscular form, all using forms known to those of ordinary skill in the pharmaceutical arts. In general, the preferred form of administration is oral. An effective but non-toxic amount of the compound is employed in the treatment of arrhythmias of the heart. The dosage regimen utilizing the compounds of the present invention is selected in accordance with a variety of factors including the type, species, age, weight, sex and medical condition of the patient; with the severity of the condition to be treated; the route of administration; the renal and hepatic function of the patient; and the particular compound employed or salt thereof. An ordinarily skilled veterinarian or physician can readily determine and prescribe the effective amount of the drug required to prevent, treat or arrest the progress of the condition.

Oral dosages of the compounds of the present invention, when used for the indicated cardiac effects, will range between about 0.1 mg per kilogram of body weight per day (mg/kg/day) to about 1000 mg/kg/day and preferably 1.0 to 100 mg/kg/day. Advantageously, the compounds of the present invention can be administered in a single daily dose or the total daily dosage can be administered in divided doses of two, three or four times daily.

In the pharmaceutical compositions and methods of the present invention, the compounds described in detail below will form the active ingredient that will typically be administered in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with conventional pharmaceutical practices.

For instance, for oral administration in the form of tablets or capsules, the active drug component can be combined with an oral non-toxic pharmaceutically acceptable inert carrier such as lactose, starch, sucrose, glucose, methylcellulose, magnesium stearate, dicalcium phosphate, calcium sulfate, mannitol, sorbitol and the like; for oral administration in liquid form, the active drug components can be combined with any oral non-toxic pharmaceutically acceptable inert carrier such as ethanol, glycerol, water, and the like. In the case of oral administration and in liquid form, suitable flavoring carriers can be added such as cherry syrup and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol and various waxes. Lubricants for use in these dosage forms include magnesium stearate, sodium benzoate, sodium acetate, sodium stearate, sodium chloride, sodium oleate and the like. Disintegrators include, without limitation, starch, methylcellulose, agar, bentonite, xanthan gum and the like.

The compounds of this invention can also be administered by intravenous route in doses ranging from 0.01 to 10 mg/kg/day.

Furthermore, it is also contemplated that the invention can be administered in an intranasal form topically via the use of suitable intranasal vehicles, or via transdermal routes, using those forms of transdermal skin patches well known to those of ordinary skill in that art. In the case of transdermal skin patch administration, daily dosage is continuous via the transdermal delivery system rather than divided, as in an oral delivery system.

The compounds of this invention exhibit antiarrythmic activity useful in the treatment of various cardiac arrhythmias. The test procedures employed to measure this activity of the compounds of the present invention are described below.

EXAMPLE 1

Guinea pigs, of either sex weighing between 200–350 g, are acutely sacrificed and the right ventricular papillary muscle is isolated. A sample of a given test compound is added using an in vitro tissue bath. Concentrations used are generally $3 \times 10^{-5}M$, but may also be as low as $3 \times 10^{-7}M$. Changes in refractory period are measured before and after adding 1 concentration (usually $3 \times 10^{-5}M$, as noted above) of a test compound to the bath. One hour is allowed for drug eguilibration. A compound is considered active (Class III) if an increase in ventricular refractory period is 25 msec or more (at $3 \times 10^{-5}M$).

| Compound | Results Concentration (M) | Change (msec) |
|---|---|---|
| H$_2$O | — | 8 |
| Disopyramide | $3 \times 10^{-5}$ | 20 |
| Clofilium | $1 \times 10^{-5}$ | 24 |
| Sotalol | $3 \times 10^{-5}$ | 35 |
| Example 2 | $3 \times 10^{-5}$ | 85 |
| Example 3 | $3 \times 10^{-5}$ | 60 |
| Example 4 | $3 \times 10^{-5}$ | 110 |
| Example 5 | $3 \times 10^{-5}$ | 80 |
| Example 7 | $1 \times 10^{-6}$ | 65 |
| Example 8 | $1 \times 10^{-5}$ | 45 |
| Example 9 | $3 \times 10^{-5}$ | 55 |
| Example 10 | $3 \times 10^{-5}$ | 40 |
| Example 12 | $3 \times 10^{-6}$ | 55 |
| Example 13 | $3 \times 10^{-5}$ | 55 |
| Example 15 | $3 \times 10^{-6}$ | 105 |

The preferred compounds of the invention are any or all of those specifically set forth in the following non-limiting examples. These compounds are not, however, to be construed as forming the only genus that is considered as the invention, and any combination of such compounds may itself form a genus. The following examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Melting points were determined on a Thomas-Hoover Unimelt Capillary Apparatus and are not corrected. Unless otherwise noted, I.R. and NMR spectra were consistent with the assigned structure.

EXAMPLE 2

4-acetamidopyridine acetate

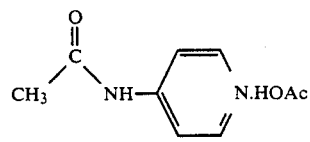

4-Aminopyridine (101.28 g) and acetic anhydride (110 g) were mixed neat and heated at 100° C. for ½ h. The solidified reaction mixture was triturated with acetone, filtered off, and washed with ether to afford 186.48 g of II as a white solid in two crops. Anal. calcd for C$_9$H$_{12}$N$_2$O$_3$: C, 55.09; H, 6.16; N, 14.26. Found: C, 55.04; H, 5.96; N, 15.22.

EXAMPLE 3

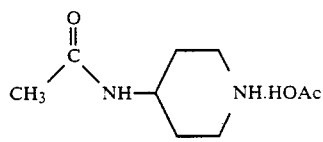

A solution of the product of Example 2 (75 g) in 750 mL acetic acid was reduced over PtO$_2$ catalyst at 60 psi hydrogen atmosphere at 60° C. for 7 hours. The solution was filtered, concentrated and triturated with ether to afford the title compound guantitatively as a white solid which was used directly in subsequent reactions.

EXAMPLE 4

1-(4-methoxyphenyl)methyl-4-acetamidopiperidine
(R$_3$ = 4-methoxy)

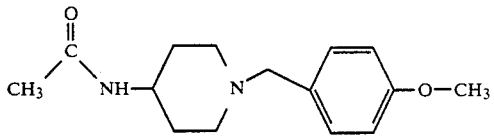

A mixture of 10 g amine acetate product of Example 3 and 13.48 g 4-methoxybenzaldehyde was hydrogenated in 100 mL ethanol over a Pt/C catalyst at room temperature for 3 hours. The reaction mixture was filtered and concentrated to give 74.0 g of the acetate salt of title compound as a white solid which was hydrolyzed directly as described in Example 5. (An alternative reductive amination procedure is described in Example 5). Conversion of a sample to the free base using aqueous base and ethyl acetate extraction provided a white solid after solvent evaporation and trituration with ether: mp 140–142° C.; Anal. calcd for C$_{15}$H$_{22}$N$_2$O$_2$: : C, 68.67; H, 8.45; N, 10.68. Found: C, 65.26; H, 8.60; N, 10.77.

EXAMPLE 5

1-(4-methoxyphenyl)methyl-4-amino piperidine
(R$_3$ = 4-methoxy)

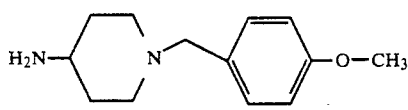

A) A solution of 50 g of the product of Example 4 ($R_3$=4-methoxy) was dissolved in 500 mL of 1.2 N HCl and heated at 100° C. and 8 h. The solution was made alkaline with 50% aq. NaOH and extracted three times with ether. The combined organic layers were washed with water and saturated brine, dried over sodium sulfate, and concentrated to give the title compound ($R_3$=4-methoxy) as 28 g of clear oil which was used without further purification.

B) (Alternative general reductive alkylation procedure) A solution of 50 mmol amine acetate III and 100 mmol of 4-methoxybenzaldehyde in 125 mL methylene chloride and 15 mL acetic acid was treated with 50 mmol of borane-pyridine complex and allowed to stir at room temperature overnight. The removal of volatiles by rotary evaporation afforded acetamide V ($R_3$=4-methoxy) as an oil which was dissolved in 300 mL of 1.2 N HCl and heated overnight on a steam bath. The cooled reaction mixture was extracted once with a 50 mL portion of ethyl acetate which was discarded. The aqueous layer was made basic with aq. NaOH and extracted three times with 50 mL ether. The combined layers were washed with water and dried over sodium sulfate. Solvent removal afforded the title compound ($R_3$=4-methoxy) as a crude oil (yield typically 60–70% for two steps) which was used directly without further purification.

EXAMPLE 6

General Acylation Procedures

A) 10 mmol of amine VI is dissolved in a mixture of 25 mL chloroform and 11 mmol of triethylamine cooled to 0° C. A solution of 11 mmol of the acyl chloride neat or dissolved in 25 mL chloroform is added dropwise and the reaction mixture is allowed to stir for 1 h. Volatiles are removed in vacuo and the residue is partitioned between dilute aqueous base and ethyl acetate. Drying of the ethyl acetate extract and evaporation leads to the crude product which is optionally purified by flash chromatography on silica gel using 92.5:7:0.5 chloroform: ethanol: ammonium hydroxide and crystallized from ethyl acetate/hexane or converted to the HCl salt using dioxane/HCl followed by recrystallization from methanol/ether.

B) A stirred solution of 10 mmol acylating acid in 25 mL chloroform is treated with 10 mmol of triethylamine followed by 10 mmol of isobutyl chloroformate. After 10 minutes at ambient temperature the amine VI was added and the reaction is allowed to stir for ½ h. The reaction mixture is washed with 10% NaOH solution and the organic layer is dried and evaporated to give a residue which is optionally purified by flash chromatography on silica gel using 92.5:7:0 5 chloroform:ethanol:ammonium hydroxide recrystallized from ethyl acetate converted to the HCl salt using dioxane/HCl followed by recrystallization from methanol/ether.

EXAMPLE 7

Preparation of Quaternary Salt

A solution of 700 mg amide I ($R_1$=Ph, $R_2$=lone pair, $R_3$=4-methoxy) in 40 mL acetone was treated with 2 mL of iodomethane. The reaction mixture was stirred for 18 h and the white crystalline precipitate was filtered off to afford 760 mg of quaternary iodine, mp 218–220° C.

EXAMPLES 8 THROUGH 24

Using the procedures of Examples 2 through 7 and making the appropriate substitutions at positions $R_1$, $R_2$, $R_3$ and $R_4$ of general structural formula I, the following products are obtained as presented in Table I, below. Table I specifies the moiety at $R_1$, $R_2$, $R_3$ and $R_4$, the number of methylenes represented by n, the compound's melting point range in degrees Celsius (where available) and the compound's elemental analysis

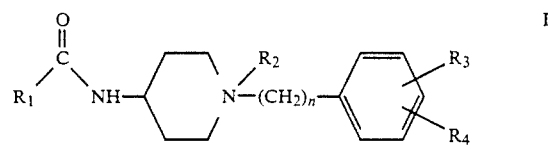

| Example | $R^1$ | $R^2$ | $R^3$, $R^4$ | n | mp, deg. C. | Analysis |
|---------|-------|-------|--------------|---|-------------|----------|
| 8 | (benzodioxole) | | 4-OCH$_3$ | 1 | 154–156 | $C_{21}H_{24}N_2O_4$ |
| 9 | (phenyl) | | 3,4(OCH$_3$)$_2$ | 1 | 154–155 | $C_{21}H_{26}N_2O_3$ |
| 10 | (phenyl) | | 4-OCH$_3$ | 2 | 171–172 | $C_{21}H_{26}N_2O_2$ |
| 11 | (phenyl) | | 4-OCH$_2$CH$_2$CH$_3$ | 1 | 155–157 | $C_{22}H_{28}N_2O_2$ |

-continued

| Example | R¹ | R² | R³, R⁴ | n | mp, deg. C. | Analysis |
|---|---|---|---|---|---|---|
| 12 | 2,6-dichlorophenyl | | 4-OCH₃ | 1 | 135–138 | $C_{20}H_{22}Cl_2N_2O_2$ |
| 13 | phenyl | CH₃ | 4-OCH₃ | 1 | 218–220 | $C_{21}H_{27}IN_2O_2$ |
| 14 | phenyl | | 4-CF₃ | 1 | 203.5–204.5 | $C_{20}H_{21}F_3N_2O$ |
| 15 | 2-methoxyphenyl | | 4-OCH₃ | 1 | oil | $C_{21}H_{26}N_2O_3$ |
| 16 | phenyl | | 4-OCH₂-(4-Cl-phenyl) | 1 | | $C_{26}H_{27}ClN_2O_2$ |
| 17 | phenyl | | | 1 | 166–168 | $C_{19}H_{22}N_2O$ |
| 18 | phenyl | | 4-OCH₃ | 1 | 157–159 | $C_{20}H_{24}N_2O_2$ |
| 19 | benzo[1,3]dioxol-5-yl | | | 1 | 162–164 | $C_{20}H_{22}N_2O_3$ |
| 20 | 2-biphenylyl | | | 1 | 143.5–145.0 | $C_{25}H_{26}N_2O$ |
| 21 | phenyl | | 4-Cl | 1 | 180–182 | $C_{19}H_{21}N_2O$ |
| 22 | cyclohexyl | | | 1 | 155–157 | $C_{19}H_{28}N_2O$ |
| 23 | cyclohexyl | | 4-OCH₃ | 1 | 170–171 | $C_{20}H_{30}N_2O_2$ |

-continued

| Example | R¹ | R² | R³, R⁴ | n | mp, deg. C. | Analysis |
|---|---|---|---|---|---|---|
| 24 | 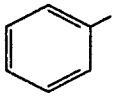 | | 4-OCH₂—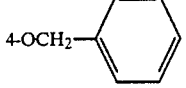 | | 148–151 | $C_{26}H_{28}N_2O_2$ |

A most preferred group of compounds consists of any or all of the following:

N-[1-[[4-[(4-chlorophenyl)methoxy] phenyl]methyl]-4-piperidinyl]benzamide;
N-[1-[[4-[(4-chlorophenyl)methyl] phenyl]methyl]-4-piperidinyl]benzamide;
N-[1-(phenylmethyl)-4-piperidinyl] benzamide;
N-[1-[(4-methoxyphenyl)methyl]-4-piperidinyl]benzamide;
N-[1-(phenylmethyl)-4-piperidinyl]-1,3-benzodioxole-5-carboxamide;
2-phenyl-N-[1-(phenylmethyl)-4-piperidinyl]benzamide;
N-[1-[(4 chlorophenyl)methyl]-4-piperidinyl]benzamide;
N-[1-[(4-methylphenyl)methyl]-4-piperidinyl]-1,3 -benzodioxole- 5-carboxamide;
N-[1-[(3,4-dimethoxyphenyl)methyl]-4-piperidinyl]benzamide;
N-[1-[2-(4-methoxyphenyl)ethyl]-4-piperidinyl]acetamide;
N-[1-[2-(4-methoxyphenyl)ethyl]-4-piperidinyl]benzamide;
N-[1-[(4-propoxyphenyl)methyl]-4-piperidinyl]benzamide;
2,6-dichloro N-[1-[(4-methoxyphenyl) methyl]-4-piperidinyl]benzamide; or
4-(benzoylamino)-1-[(4-methoxyphenyl) methyl]-1-methylpiperidinium, iodine.

While the invention has been described and illustrated with reference to certain preparative embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the mammal being treated for severity of cardiac arrhythmia, dosage-related adverse effects, if any, and analogous considerations. Likewise, the specific pharmacological responses observed may vary according to and depending upon the particular active compounds selected or whether there are present certain pharmaceutical carriers, as well as the type of formulation and mode of administration employed, and such expected variations for differences in the results are contemplated in accordance with the objects and practices of the present invention. It is intended, therefore, that the invention be limited only by the scope of the claims which follow, and that such claims be interpreted as broadly as is reasonable.

What is claimed is:

1. A compound of the formula

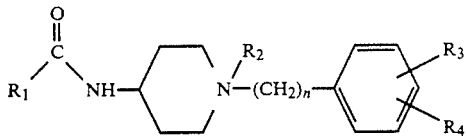

or the pharmaceutically acceptable non-toxic salts thereof, or the hydrated forms thereof, wherein $R^1$ benzodioxolyl; $R^2$ is absent or is an alkyl from 1–10 carbon atoms; n is an integer of from zero to three; and $R^3$ and $R^4$ are independently hydrogen, halogen, halogen substituted alkyl of from one to ten carbon atoms in length, arylalkoxy of from one to ten carbon atoms in length wherein aryl may be substituted by halogen or alkyl of one to ten carbon atoms in length, or alkoxy of one to ten carbon atoms in length.

2. The compound as claimed in claim 1, wherein n is one.

3. The compound as claimed in claim 1, wherein $R^3$ is alkoxy.

4. The compound as claimed in claim 2, wherein $R^3$ is methoxy.

5. The compound as claimed in claim 3, wherein $R^3$ is para-methoxy.

6. The compound as claimed in claim 1, wherein $R^4$ is hydrogen.

7. A compound as claimed in claim 1, of the formula

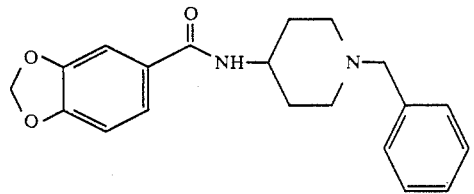

8. A compound as claimed in claim 1, of the formula

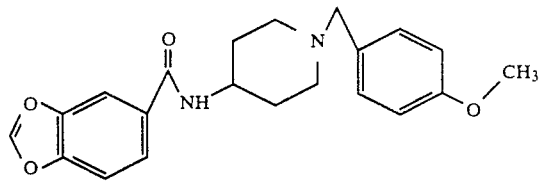

9. A pharmaceutical composition useful for regulating cardiac arrhythmias comprising an effective amount of a compound according to claim 1, together with one or more non-toxic pharmaceutically acceptable carriers.

10. The composition as claimed in claim 9, wherein said compound is N-[1-(phenylmethyl)-4-piperidinyl]-1,3-benzodioxole-5-carboxamide.

11. The composition as claimed in claim 9, wherein said compound is N-[1-[(4-methylphenyl)methyl]-4-piperidinyl]-1,3-benzodioxole-5-carboxamide.

12. A method of regulating cardiac arrhythmias in a mammal, comprising administering to said mammal a pharmacologically effective amount of a compound as claimed in claim 1.

13. The method as claimed in claim 12, wherein said compound is N-[1-(phenylmethyl)-4-piperidinyl]-1,3-benzodioxole-5-carboxamide.

14. The method as claimed in claim 12, wherein said compound is N-[1-[(4-methoxyphenyl)methyl]-4-piperidinyl]-1,3-benzodioxole-5-carboxamide.

15. A method of prolonging repolarization of cardiac cells during a cardiac action potential, comprising administering to such mammal a pharmacologically effective amount of a compound as claimed in claim 1.

* * * * *

UNITED STATES PATENT AND TRADEMARK OFFICE
CERTIFICATE OF CORRECTION

PATENT NO. : 5,028,616

DATED : Jul. 2, 1991

INVENTOR(S) : Desai et al.

It is certified that error appears in the above-identified patent and that said Letters Patent is hereby corrected as shown below:

Column 1, line 51, reading "ten carbon atoms, phenyl" should read -- ten carbon atoms, phenyl, --.

Column 1, line 53, reading "atoms cycloalkyl" should read -- atoms, cycloalkyl --.

Column 5, line 33, reading "drug eguilibration." should read -- drug equilibration. --.

Column 6, line 35, reading "compound guantitatively" should read -- compound quantitatively --.

Column 11, lines 19-20, reading "N-[1[[4[(4-chlorophenyl) methyl] phenyl]methyl]4-piperidinyl]benzamide;" should be removed.

Signed and Sealed this

Twenty-third Day of February, 1993

Attest:

STEPHEN G. KUNIN

Attesting Officer

Acting Commissioner of Patents and Trademarks